United States Patent
Youn et al.

(10) Patent No.: US 12,243,706 B1
(45) Date of Patent: Mar. 4, 2025

(54) HIGH-VOLTAGE X-RAY TANK WITH MINIATURIZED SHIELDING STRUCTURE

(71) Applicant: FSK Co., Ltd., Gimpo-si (KR)

(72) Inventors: Ju Seon Youn, Seoul (KR); Ha Yeon Youn, Seoul (KR); Ronald Viola, Pittsford, NY (US)

(73) Assignee: FSK Co., Ltd., Gimpo-si (KR)

( * ) Notice: Subject to any disclaimer, the term of this patent is extended or adjusted under 35 U.S.C. 154(b) by 0 days.

(21) Appl. No.: 18/819,334

(22) Filed: Aug. 29, 2024

(30) Foreign Application Priority Data

Aug. 31, 2023 (KR) ........................ 10-2023-0115559

(51) Int. Cl.
*H01J 35/16* (2006.01)
*A61B 6/00* (2024.01)
*H01J 35/18* (2006.01)

(52) U.S. Cl.
CPC ............ *H01J 35/16* (2013.01); *H01J 35/165* (2013.01); *H01J 35/18* (2013.01); *A61B 6/44* (2013.01); *H01J 2235/163* (2013.01); *H01J 2235/166* (2013.01)

(58) Field of Classification Search
CPC .......... H01J 35/16; H01J 35/165; H01J 35/18; H01J 2235/163; H01J 2235/166
See application file for complete search history.

(56) References Cited

U.S. PATENT DOCUMENTS

| | | | | |
|---|---|---|---|---|
| 5,056,126 A | * | 10/1991 | Klostermann | H05G 1/025 378/127 |
| 2021/0148840 A1 | * | 5/2021 | Cui | H01J 35/18 |

FOREIGN PATENT DOCUMENTS

| | | |
|---|---|---|
| KR | 10-1211617 B1 | 12/2012 |
| KR | 10-2019-0005433 A | 1/2019 |
| KR | 10-2021-0126481 A | 10/2021 |
| KR | 10-2022-0157243 A | 11/2022 |

OTHER PUBLICATIONS

JP 2007-080568 A and its English translation (Year: 2007).*
Request for the Submission of an Opinion issued Nov. 24, 2023 in Korean Patent Application No. 10-2023-0115559.
Written Decision on Registration issued Feb. 15, 2024 in Korean Patent Application No. 10-2023-0115559.

* cited by examiner

*Primary Examiner* — Chih-Cheng Kao
(74) *Attorney, Agent, or Firm* — Sughrue Mion, PLLC

(57) ABSTRACT

Disclosed is a high-voltage X-ray tank with a miniaturized shielding structure which includes an X-ray shielding part having a cylindrical structure in which an X-ray tube for radiating X-rays is accommodated and an X-ray radiation port is formed in one side surface thereof, a main block body having a box-shaped structure in which the X-ray shielding part is mounted on one side surface thereof and which is electrically connected to the X-ray shielding part, and a lens part having a structure which is mounted on the one side surface of the X-ray shielding part and focuses X-rays radiated through the X-ray radiation port on a preset position. According to the present invention, the high-voltage X-ray tank, in which insulating and shielding performance is improved and which has an ultra-small and ultra-light-shielding structure based on the improved insulating and shielding performance, can be provided.

4 Claims, 6 Drawing Sheets

HIGH-VOLTAGE X-RAY TANK WITH MINIATURIZED SHIELDING STRUCTURE

CROSS-REFERENCE TO RELATED APPLICATION(S)

This application claims priority from Korean Patent Application No. 10-2023-0115559, filed on Aug. 31, 2023, in the Korean Intellectual Property Office, the disclosure of which is incorporated herein by reference in its entirety.

BACKGROUND

1. Field

The present invention relates to a high-voltage X-ray tank, and more specifically, to a high-voltage X-ray tank with a miniaturized and lightened shielding structure.

2. Description of Related Art

In general, X-ray generators are applied to and widely used in various testing devices or diagnostic devices for medical diagnostics, non-destructive tests, chemical analysis, and the like.

Meanwhile, in order to generate X-rays, high voltage is required, and conventionally, insulation technology using an insulating oil or insulating gas, mold technology, or the like is used to secure electrical insulation (see FIG. 1).

The insulation technology using the mold technology has an advantage of securing insulation even with a small size, but there is a problem that many voids are formed during molding and insulation efficiency is reduced.

In addition, when an apparatus using X-rays is used, efforts to block X-rays harmful to the human body are very important. Currently, a shielding material most commonly used when a small X-ray tube is manufactured is lead, and since lead can be formed into a thin sheet type, processability is good. However, since lead is a heavy metal, there is a problem that it is harmful to the environment and the human body.

Meanwhile, in the case of metals with high specific gravity such as tungsten which has been proposed as a material that can replace lead, due to the conductivity of tungsten, there is a problem that an electrical separation is not easy in a structure which should be electrically insulated. Accordingly, as an insulating tank (bath) for insulating an X-ray tube and a shielding material surrounding an outer portion of the insulating tank are provided, there is a problem that a size and a weight of an X-ray generator increase.

Accordingly, there is a need to solve the problem according to the conventional technology.

RELATED ART

Patent Document (Patent Document 1) Korean Registered Patent Publication No. 10-252003 (Registration date: Apr. 5, 2023)

SUMMARY

The purpose of the present invention is to provide a high-voltage X-ray tank in which insulating and shielding performance is improved and which has an ultra-small and ultra-light shielding structure based on the improved insulating and shielding performance.

A high-voltage X-ray tank in accordance with one aspect of the present invention for achieving the problem includes an X-ray shielding part having a cylindrical structure in which an X-ray tube for radiating X-rays is accommodated and an X-ray radiation port is formed in one side surface thereof, a main block body having a box-shaped structure in which the X-ray shielding part is mounted on one side surface thereof and which is electrically connected to the X-ray shielding part, and a lens part having a structure which is mounted on the one side surface of the X-ray shielding part and focuses X-rays radiated through the X-ray radiation port on a preset position.

In one embodiment of the present invention, the X-ray shielding part may include a central shielding part having a hollow cylindrical structure, in which the X-ray radiation port is formed at a center of one side surface thereof, and formed of a shielding lead material, wherein the X-ray tube is mounted in the hollow structure, and both end portions of the central shielding part are open, a left shielding part which is mounted on a left end of the central shielding part as a detachable structure, is formed of a shielding lead material, and has a cylindrical structure having a side surface structure continuing from a side surface of the central shielding part, and a right shielding part which is mounted on a right end of the central shielding part as a detachable structure, is formed of a shielding lead material, and has a cylindrical structure having a side surface structure continuing from the side surface of the central shielding part.

In one embodiment of the present invention, the X-ray shielding part may include circuit connectors which are mounted at centers of the other side surfaces of the left shielding part and the right shielding part and have structures electrically connected to the main block body and fixing brackets which are mounted as structures surrounding an outer circumferential surface of the central shielding part to fix the central shielding part to one side surface of the main block body.

In one embodiment of the present invention, the lens part may include a lens fixing plate having a rectangular plate-shaped structure which has the same size and shape as the one side surface of the main block body and in which a lens fastener is mounted at a location corresponding to the X-ray radiation port at the center of the one side surface of the central shielding part, the lens fastener which is mounted at a center of one side of the lens fixing plate and in which a lens is mounted, and a block fastener which is mounted on the other side surface of the lens fixing plate, is mounted in a left-right symmetrical shape, and has a structure fixed to the one side surface of the main block body.

In one embodiment of the present invention, the block fastener may have a structure to be inserted into the main block body in an inward direction or withdrawn therefrom, an accommodation space, which surrounds an outer surface of the X-ray shielding part and accommodates the X-ray shielding part, may be formed at one side of the main block body, and the lens fixing plate may have a structure for sealing the accommodation space formed at the one side of the main block body.

In one embodiment of the present invention, the main block body may include an emergency controller which is mounted in the main block body, operates the block fastener to accommodate the X-ray shielding part in the accommodation space of the main block body, controls the lens fixing plate to seal and shield the accommodation space, and operates the emergency filling part when a preset emergency situation is detected and an emergency filling part mounted in the main block body and having a structure which is operated by a control signal of the emergency controller to fill the accommodation space of the main block body with an X-ray shielding material.

DETAILED DESCRIPTION

Hereinafter, exemplary embodiments of the present invention will be described in more detail with reference to the accompanying drawings. Moreover, terms and words used in the present specification and claims should not be interpreted as being limited to commonly used meanings or meanings in dictionaries and should be interpreted as having meanings and concepts which are consistent with the technological spirit of the invention.

Throughout this specification, when a first member is referred to as being "on" a second member, the first member is in contact with the second member or a third member is interposed between the two members. Throughout this specification, when a certain part "includes" a certain component, other components are not excluded unless explicitly described otherwise, and other components may further be included therein.

Figure 1:
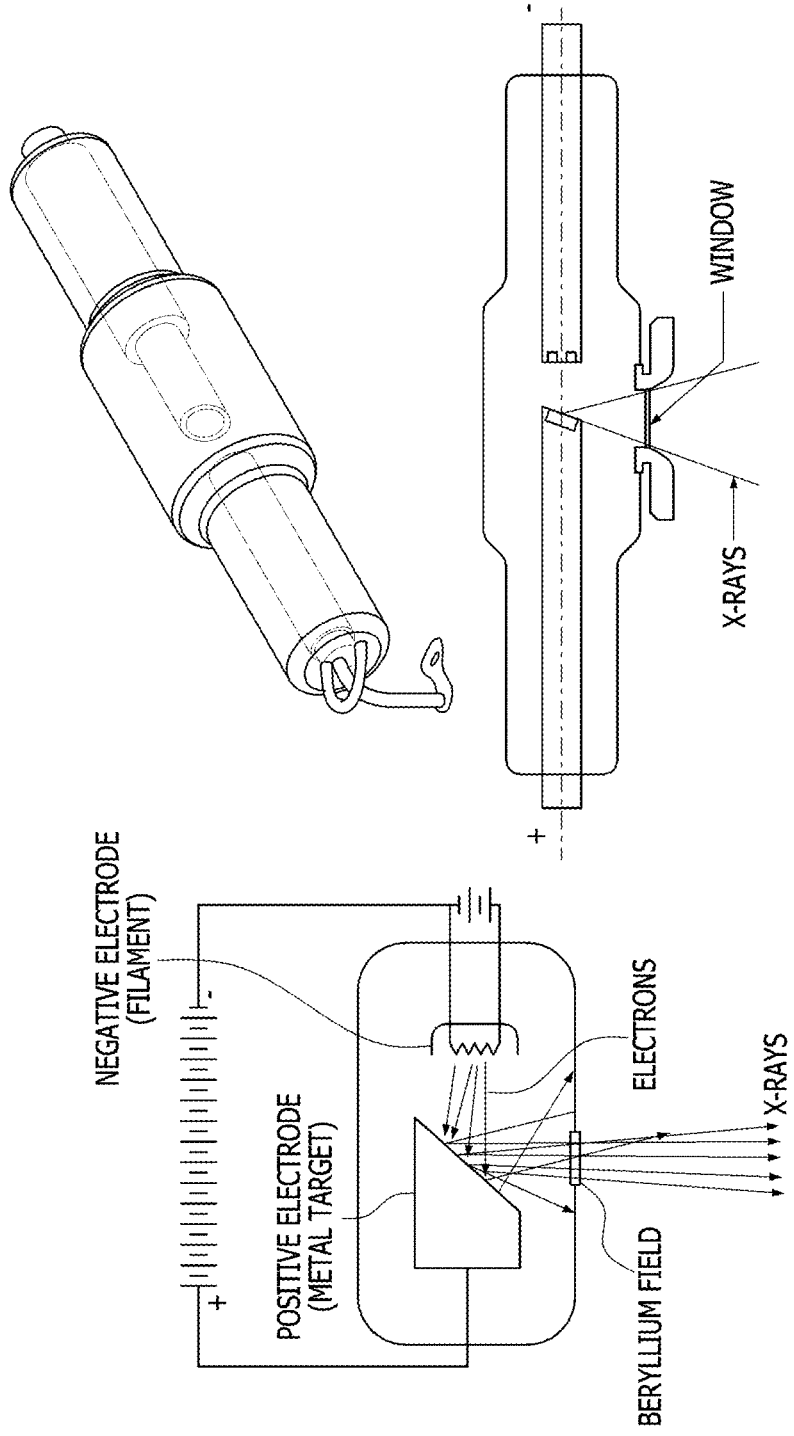
FIG. 1 is a picture showing an X-ray generator according to a conventional technology.
Figure 2:
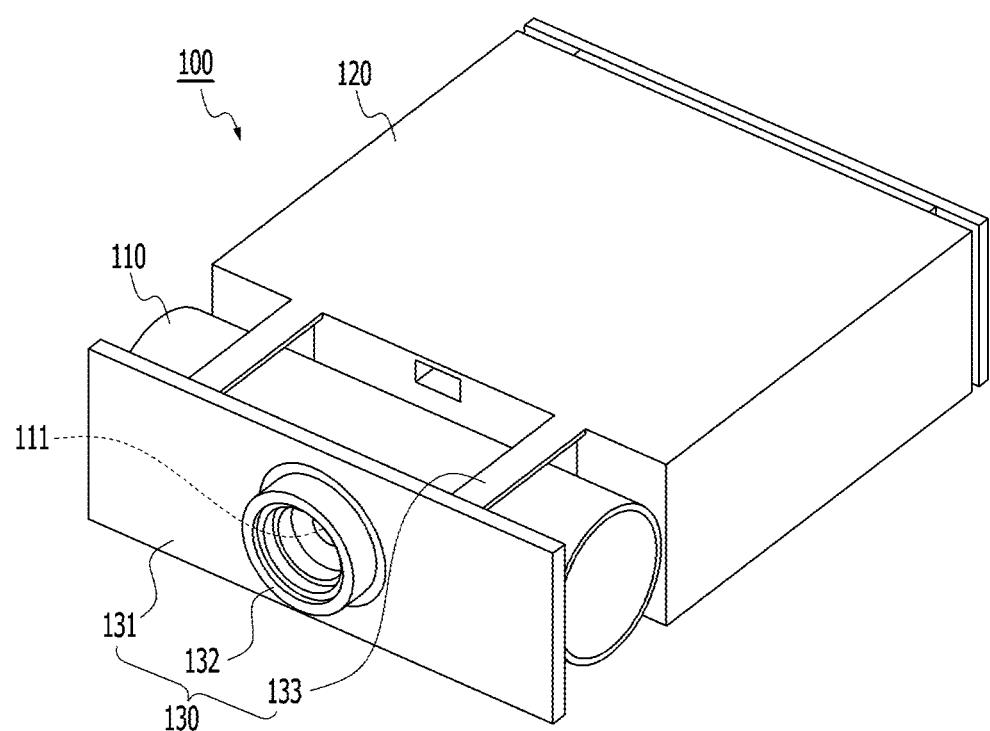
FIG. 2 is a perspective view illustrating a high-voltage X-ray tank according to one embodiment of the present invention.

FIG. 2 is a perspective view illustrating a high-voltage X-ray tank according to one embodiment of the present invention.

Referring to FIG. 2, as a high-voltage X-ray tank 100 according to the present embodiment includes an X-ray shielding part 110, a main block body 120, and a lens part 130 which are formed in a specific structure, insulating and shielding performance can be improved, and the high-voltage X-ray tank having an ultra-small and ultra-light-shielding structure based on the improved insulating and shielding performance can be provided.

Hereinafter, components constituting the high-voltage X-ray tank 100 according to the present embodiment will be described with reference to the accompanying drawings.

Figure 3:
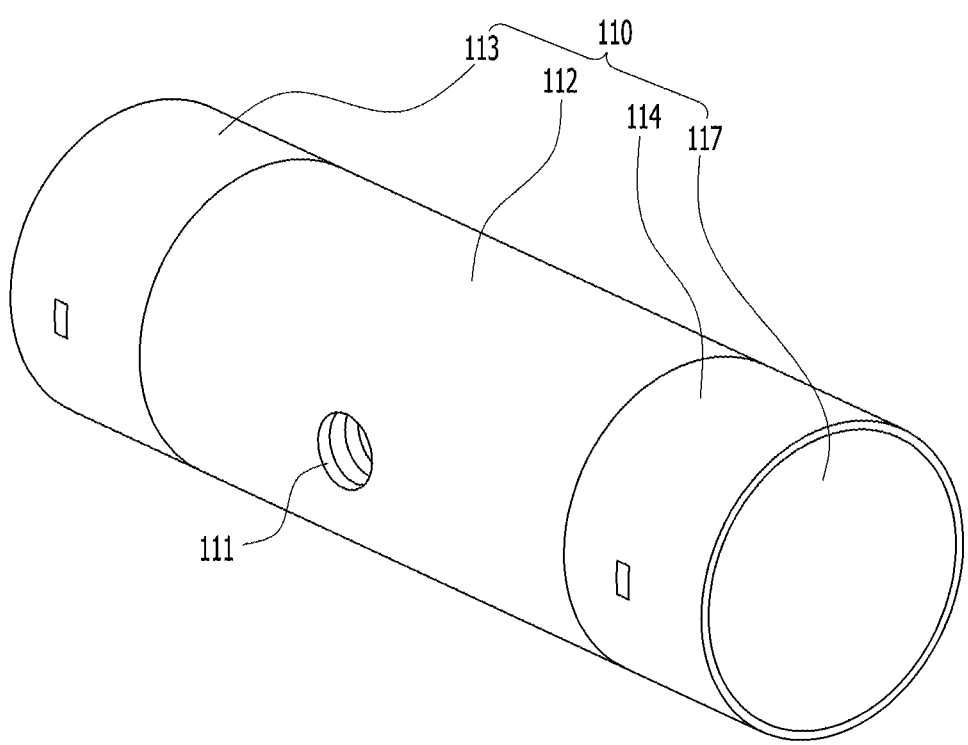
FIG. 3 is a perspective view illustrating an X-ray shielding part of the high-voltage X-ray tank illustrated in FIG. 2.
Figure 4:
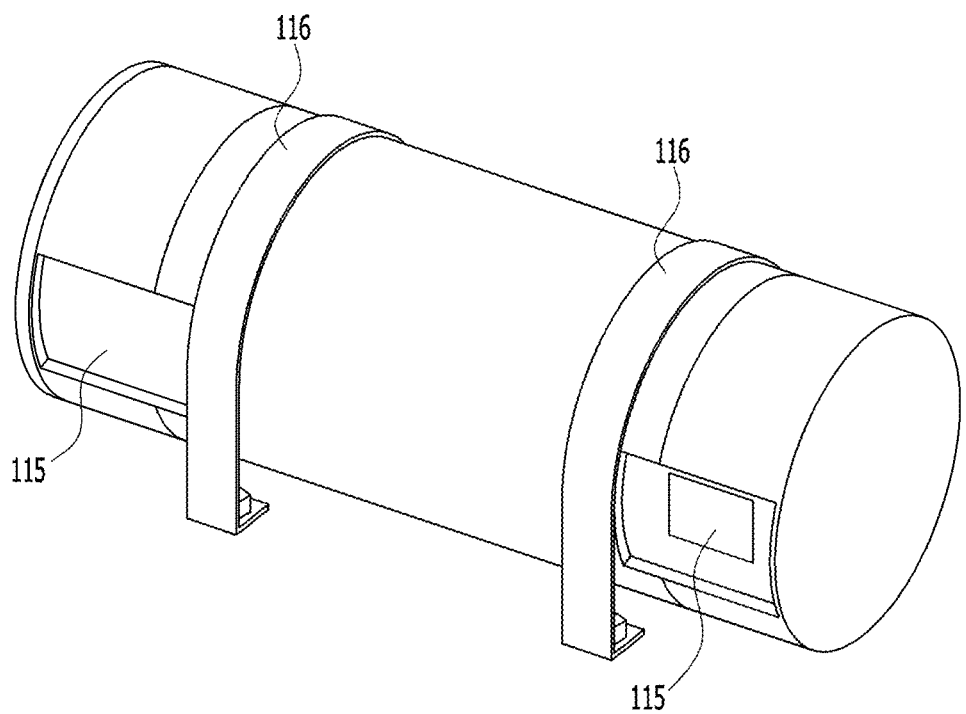
FIG. 4 is a perspective view illustrating a rear side of the X-ray shielding part when a fixing bracket is mounted on the X-ray shielding part illustrated in FIG. 3.

FIG. 3 is a perspective view illustrating the X-ray shielding part of the high-voltage X-ray tank illustrated in FIG. 2, and FIG. 4 is a perspective view illustrating a rear side of the X-ray shielding part when a fixing bracket is mounted on the X-ray shielding part illustrated in FIG. 3.

Referring to FIGS. 2 to 4, the X-ray shielding part 110 according to the present embodiment has a cylindrical structure in which an X-ray tube for radiating X-rays is accommodated and an X-ray radiation port 111 is formed in one side surface thereof.

The main block body 120 according to the present embodiment has a box-shaped structure in which the X-ray shielding part 110 is mounted on one side surface and which is electrically connected to the X-ray shielding part 110.

The lens part 130 according to the present embodiment has a structure which is mounted on one side surface of the X-ray shielding part 110 and focuses X-rays radiated through the X-ray radiation port 111 on a preset position.

Specifically, the X-ray shielding part 110 may be a component including a central shielding part 112, a left shielding part 113, and a right shielding part 114 which are formed in a specific structure. The central shielding part 112 has a hollow cylindrical structure in which the X-ray radiation port 111 is formed at a center of one side surface thereof and is formed of a shielding lead material, the X-ray tube is mounted in the hollow structure, and both end portions thereof are open. The left shielding part 113 is mounted on a left end of the central shielding part 112 as a detachable structure, is formed of a shielding lead material, and has a cylindrical structure having a side surface structure continued from a side surface of the central shielding part 112. The right shielding part 114 is mounted on a right end of the central shielding part 112 as a detachable structure, is formed of a shielding lead material, and has a cylindrical structure having a side surface structure continuing from the side surface of the central shielding part 112. In some cases, an opening and closing part 117 having a structure capable of opening or sealing an internal space may be mounted on one side surface of the right shielding part 114. The X-ray tube mounted in the X-ray shielding part 110 may be replaced or maintained through the opening and closing part 117.

As illustrated in FIG. 4, the X-ray shielding part 110 according to the present embodiment may be a component including circuit connectors 115 and fixing brackets 116 which are formed in a specific structure.

Specifically, the circuit connectors 115 of the X-ray shielding part 110 are mounted at centers of the other side surfaces of the left shielding part 113 and the right shielding part 114 and have structures electrically connected to the main block body 120. In addition, the fixing brackets 116 of the X-ray shielding part 110 are mounted as structures surrounding an outer circumferential surface of the central shielding part 112 to fix the central shielding part 112 to one side surface of the main block body 120.

Meanwhile, the lens part 130 according to the present embodiment may be a component including a lens fixing plate 131, a lens fastener 132, and a block fastener 133 which are formed in a specific structure. Specifically, the lens fixing plate 131 has a rectangular plate-shaped structure which has the same size and shape as one side surface of the main block body 120 and in which the lens fastener 132 is mounted at a location corresponding to the X-ray radiation port 111 at the center of one side surface. The lens fastener 132 is a component which is mounted at a center of one side of the lens fixing plate 131 and in which a lens is mounted. The block fastener 133 is a component mounted on the other side surface of the lens fixing plate 131, is mounted in a left-right symmetrical shape, and has a structure fixed to one side surface of the main block body 120.

Figure 5:
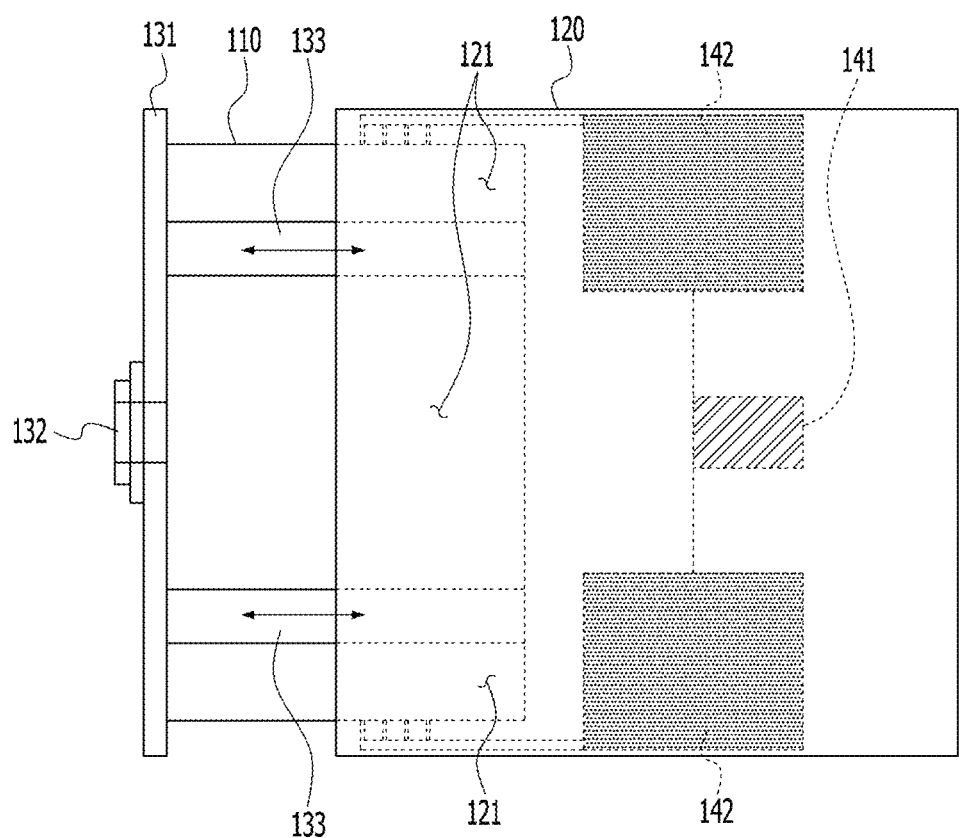
FIG. 5 is a plan view illustrating the high-voltage X-ray tank illustrated in FIG. 2.
Figure 6:
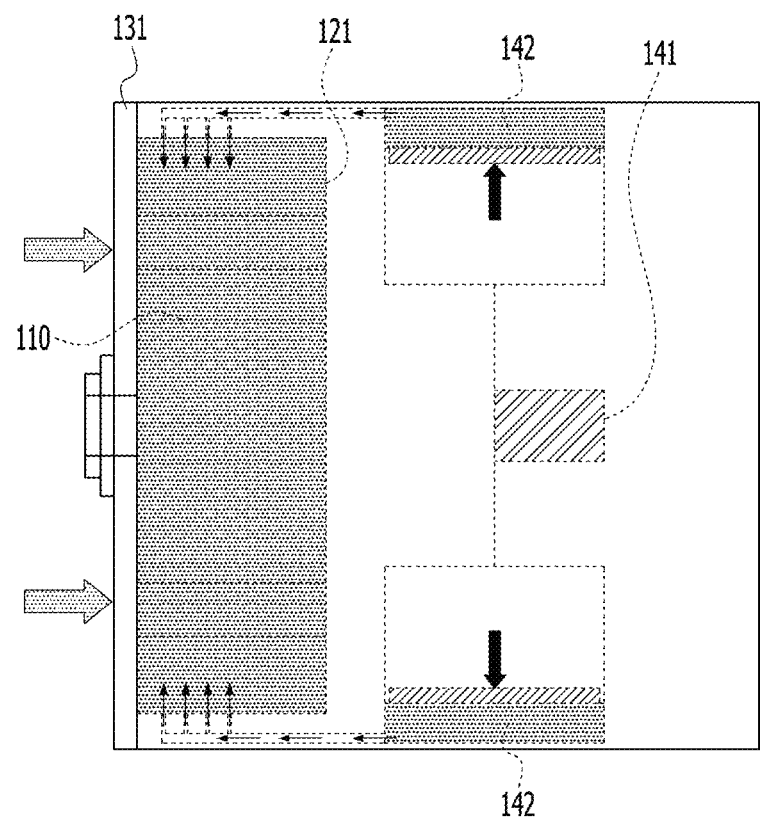
FIG. 6 is a plan view illustrating a state in which the X-ray shielding part of the high-voltage X-ray tank is accommodated in an accommodation space of a main block body, and the main block body is sealed, shielded, and filled with an X-ray shielding material.

FIG. 5 is a plan view illustrating the high-voltage X-ray tank illustrated in FIG. 2, and FIG. 6 is a plan view illustrating a state in which the X-ray shielding part of the high-voltage X-ray tank is accommodated in an accommodation space of the main block body, and the main block body is sealed, shielded, and filled with an X-ray shielding material.

Referring to the drawings, the block fastener 133 according to the present embodiment may have a structure to be inserted into the main block body 120 in an inward direction or withdrawn therefrom.

In this case, an accommodation space 121 which surrounds an outer surface of the X-ray shielding part 110 and accommodates the X-ray shielding part 110 may be formed at one side of the main block body 120. In addition, the lens fixing plate 131 may have a structure capable of sealing the accommodation space 121 formed at one side of the main block body 120.

In some cases, as illustrated in FIG. 6, the main block body 120 may be a component including an emergency controller 141 and an emergency filling part 142 which perform specific roles.

Specifically, the emergency controller 141 of the main block body 120 is a component mounted in the main block body 120, and may operate the block fastener 133 to accommodate the X-ray shielding part 110 in the accommodation space 121 of the main block body 120, control the lens fixing plate 131 to seal and shield the accommodation space 121, and operate the emergency filling part 142 when a preset emergency situation is detected. In addition, the emergency filling part 142 is a component mounted in the main block body 120 and has a structure which is operated by a control signal of the emergency controller 141 to fill the accommodation space 121 of the main block body 120 with an X-ray shielding material.

According to the present embodiment including these components, as the X-ray shielding part 110 surrounding the X-ray tube inserted into the main block body 120 is sealed, and the main block body 120 is filled with the X-ray shielding material when an emergency situation having a preset condition is detected, X-rays can be prevented from leaking to the outside of the X-ray tube, and thus an accident caused by X-ray leakage can be prevented in advance as a result.

As described above, a high-voltage X-ray tank of the present invention has an X-ray shielding part, a main block body, and a lens part which are formed in a specific structure, and therefore insulating and shielding performance can be improved, and has an ultra-small and ultra-light-shielding structure based on the improved insulating and shielding performance.

In addition, according to the high-voltage X-ray tank of the present invention, as a lens part including a lens fixing plate, a lens fastener, and a block fastener which are formed in a specific structure is provided, a main block body having a specific structure is provided, and an emergency controller and an emergency filling part for performing specific roles are provided, when an emergency situation having a preset condition is detected, an X-ray shielding part surrounding an X-ray tube is inserted into the main block body, the main block body is sealed, and the main block body is filled with an X-ray shielding material, thereby preventing X-rays from leaking to the outside of the X-ray tube, and thus an accident due to the X-ray leakage can be prevented in advance as a result.

In the above detailed description of the present invention, only specific embodiments according thereto have been described. However, it should be understood that the present invention is not limited to the specific embodiments described in the detailed description, and all changes, equivalents, and substitutes falling within the spirit and technical scope of the present invention are encompassed in the present invention.

Accordingly, the present invention is not limited to the above-described specific embodiments and descriptions and may be variously modified by those skilled in the art without departing from the gist of the invention claimed by the appended claims, and the modifications are within the scope of the claims.

What is claimed is:

1. A high-voltage X-ray tank comprising:
an X-ray shielding part (110) having a cylindrical structure in which an X-ray tube for radiating X-rays is accommodated and an X-ray radiation port (111) is formed in one side surface thereof;
a main block body (120) having a box-shaped structure in which the X-ray shielding part (110) is mounted on one side surface thereof and which is electrically connected to the X-ray shielding part (110); and
a lens part (130) having a structure which is mounted on the one side surface of the X-ray shielding part (110) and focuses X-rays radiated through the X-ray radiation port (111) on a preset position,
wherein the X-ray shielding part (110) includes a central shielding part (112) having a hollow cylindrical structure, in which the X-ray radiation port (111) is formed at a center of one side surface thereof, and formed of a shielding lead material, wherein the X-ray tube is mounted in the hollow structure, and both end portions of the central shielding part (112) are open,
a left shielding part (113) which is mounted on a left end of the central shielding part (112) as a detachable structure, is formed of a shielding lead material, and has a cylindrical structure having a side surface structure continuing from a side surface of the central shielding part (112),
a right shielding part (114) which is mounted on a right end of the central shielding part (112) as a detachable structure, is formed of a shielding lead material, and has a cylindrical structure having a side surface structure continuing from the side surface of the central shielding part (112);
circuit connectors (115) which are mounted at centers of the other side surfaces of the left shielding part (113) and the right shielding part (114) and have structures electrically connected to the main block body (120); and
fixing brackets (116) which are mounted as structures surrounding an outer circumferential surface of the central shielding part (112) to fix the central shielding part (112) to one side surface of the main block body (120).

2. The high-voltage X-ray tank of claim 1, wherein the lens part (130) includes:
a lens fixing plate (131) having a rectangular plate-shaped structure which has the same size and shape as the one side surface of the main block body (120) and in which a lens fastener (132) is mounted at a location corresponding to the X-ray radiation port (111) at the center of the one side surface of the central shielding part (112);
the lens fastener (132) which is mounted at a center of one side of the lens fixing plate (131) and in which a lens is mounted; and
a block fastener (133) which is mounted on the other side surface of the lens fixing plate (131), is mounted in a left-right symmetrical shape, and has a structure fixed to the one side surface of the main block body (120).

3. The high-voltage X-ray tank of claim 2, wherein:
the block fastener (133) has a structure to be inserted into the main block body (120) in an inward direction or withdrawn therefrom;
an accommodation space (121), which surrounds an outer surface of the X-ray shielding part (110) and accommodates the X-ray shielding part (110), is formed at one side of the main block body (120); and
the lens fixing plate (131) has a structure for sealing the accommodation space (121) formed at the one side of the main block body (120).

4. The high-voltage X-ray tank of claim 3, wherein the main block body (120) includes:
an emergency controller (141) which is mounted in the main block body (120), operates the block fastener (133) to accommodate the X-ray shielding part (110) in the accommodation space (121) of the main block body (120), controls the lens fixing plate (131) to seal and shield the accommodation space (121), and operates an emergency filling part (142) when a preset emergency situation is detected; and
the emergency filling part (142) mounted in the main block body (120) and having a structure which is operated by a control signal of the emergency controller (141) to fill the accommodation space (121) of the main block body (120) with an X-ray shielding material.

\* \* \* \* \*